United States Patent [19]

Blanchard et al.

[11] Patent Number: 5,556,984
[45] Date of Patent: Sep. 17, 1996

[54] AMMOXIDATION OF SATURATED HYDROCARBONS

[75] Inventors: Gilbert Blanchard, Le Plessis Belleville; Elisabeth Bordes, Vemars; Gilbert Ferre, Livry Gargan, all of France

[73] Assignee: Rhone-Poulenc Chimie, Courbevoie Cedex, France

[21] Appl. No.: 216,514

[22] Filed: Mar. 23, 1994

Related U.S. Application Data

[63] Continuation of Ser. No. 909,184, Jul. 6, 1992, abandoned.

[30] Foreign Application Priority Data

Jul. 4, 1991 [FR] France ................................ 91 08643

[51] Int. Cl.$^6$ .............................................. C07C 253/24
[52] U.S. Cl. .............................................................. 558/319
[58] Field of Search ............................................... 558/319

[56] References Cited

U.S. PATENT DOCUMENTS

| | | | |
|---|---|---|---|
| 3,365,482 | 1/1968 | Khoobiar | 558/319 |
| 3,395,159 | 7/1968 | Levine | 558/319 X |
| 3,433,823 | 3/1969 | McMahon | 558/319 |
| 3,670,009 | 6/1972 | Taylor | 558/319 |
| 3,678,090 | 7/1972 | Taylor | 558/319 |
| 3,686,267 | 8/1972 | Taylor | 558/319 |
| 3,833,638 | 9/1974 | Knox et al. | 558/319 |
| 3,927,007 | 12/1975 | Lussling et al. | 558/319 X |
| 4,309,361 | 1/1982 | Suresh et al. | 558/319 |
| 4,618,593 | 10/1986 | Sasaki et al. | 558/319 X |
| 4,760,159 | 7/1988 | Suresh et al. | 558/319 |
| 4,767,739 | 8/1988 | Glaeser et al. | 558/319 X |
| 4,774,352 | 9/1988 | Sasaki et al. | 558/319 X |
| 4,783,545 | 11/1988 | Glaeser et al. | 558/319 |
| 4,801,568 | 1/1989 | Brazdil, Jr. et al. | 558/319 X |
| 4,801,727 | 1/1989 | Glaeser et al. | 558/319 |
| 4,814,478 | 3/1989 | Glaeser et al. | 558/319 |
| 4,866,024 | 9/1989 | Brazdil, Jr. et al. | 558/319 X |
| 4,871,706 | 10/1989 | Brazdil, Jr. et al. | 558/319 X |
| 4,877,764 | 10/1989 | Glaeser et al. | 558/319 X |
| 4,883,896 | 11/1989 | Glaeser et al. | 558/319 |
| 4,888,438 | 12/1989 | Glaeser et al. | 558/319 |
| 4,978,764 | 12/1990 | Seely et al. | 558/319 |
| 5,008,427 | 4/1991 | Brazdil, Jr. et al. | 558/319 |

FOREIGN PATENT DOCUMENTS

| | | | |
|---|---|---|---|
| 0282314 | 9/1988 | European Pat. Off. | |
| 0342777 | 11/1989 | European Pat. Off. | |
| 0344884 | 12/1989 | European Pat. Off. | |
| 0524895 | 1/1993 | European Pat. Off. | 518/319 |
| 1462595 | 7/1966 | France | |
| 1488234 | 6/1967 | France | |
| 2027238 | 9/1970 | France | |
| 2072334 | 9/1971 | France | |
| 2072399 | 9/1971 | France | |
| 2119492 | 4/1972 | France | |
| 2119779 | 4/1972 | France | |
| 1337759 | 11/1973 | United Kingdom | |
| 1336136 | 11/1973 | United Kingdom | |
| 1336135 | 11/1973 | United Kingdom | |

OTHER PUBLICATIONS

"Chemistry Letters" pp. 2173–2176, 1989, Kim et al.
Japanese Patent Abstract No. JP3058961, Application No. JP890191317, Published May 27, 1991, vol. 015206.
Arzu B. Azimov, et al, *Journal of Catalysis*, "Dehydrogenation" Mechanism for Ammoxidation of Alkylaromatic Hydrocarbons, vol. 127, pp. 354–365, (1991).

*Primary Examiner*—Robert W. Ramsuer
*Attorney, Agent, or Firm*—Burns, Doane, Swecker & Mathis, L.L.P.

[57] ABSTRACT

The saturated hydrocarbons, typically alkanes having from 3 to 12 carbon atoms, e.g., propane, are selectively ammoxidized into $\alpha,\beta$-unsaturated nitriles and olefins, e.g., acrylonitrile and propylene, by reacting such alkanes with ammonia and oxygen, in vapor phase and in the presence of a solid catalyst, such solid catalyst including a catalytically effective amount of an active catalytic phase which comprises molybdenum, oxygen and at least one element selected from among the alkaline earth metals, Mn, Fe, U, La, Co, Ni, Zn, Ag, Cd, W, Zr, Pb, Te, Ga, Al, B, Nb and Ta.

18 Claims, 1 Drawing Sheet

AMMOXIDATION OF SATURATED HYDROCARBONS

This application is a continuation, of application Ser. No. 07/909,184, filed Jul. 6, 1992 now abandoned.

BACKGROUND OF THE INVENTION

1. Field of the Invention

The present invention relates to the ammoxidation of saturated hydrocarbons, and more especially, to the conversion of alkanes into a mixture comprising $\alpha,\beta$-unsaturated nitriles.

2. Description of the Prior Art

It is well known to this art that a variety of techniques exist for the ammoxidation of olefins and, in particular, for the ammoxidation of propylene. However, although the saturated hydrocarbons, which are more widely commercially available, are raw materials which are of greater interest from the standpoint of economics, they are also well known not to exhibit a comparable reactivity in this type of reaction for forming, particularly, $\alpha,\beta$-unsaturated nitriles.

One of the difficulties encountered in the ammoxidation of saturated hydrocarbons is the requirement for catalysts capable of dehydrogenating the saturated hydrocarbon under conditions which minimize or suppress the combustion of ammonia and/or that of the hydrocarbon, while at the same time ensuring a reasonable selectivity either for the $\alpha,\beta$-unsaturated nitrile (the desired final product), for example for acrylonitrile from propane, or for final products which are commercially attractive (the aforesaid nitrile and olefin), for example for acrylonitrile and propylene from a propane starting material.

U.S. Pat. No. 3,365,482 describes ammoxidizing isobutane, in particular into methacrylonitrile, on a catalyst based on molybdenum deposited onto eta-alumina, doped with antimony at 508° C. The starting material is a gaseous mixture containing isobutane, air, ammonia and water vapor (1.0/4.5/1.0/12.5); the selectivity for methacrylonitrile attains a value of 49% with an isobutane conversion of 22%.

Starting with a gaseous mixture of propane/air/ammonia/water vapor (1.0/4.7/0.67/12.8) and using the same catalyst at 550° C., the selectivity for acrylonitrile decreases to 15% with a propane conversion of 29%.

French Patent No. 2,027,238 (in part corresponding to U.S. Pat. No. 3,670,009) describes a vapor phase process for the ammoxidation of saturated hydrocarbons at a temperature above 500° C. employing a solid catalyst, notably consisting essentially of tin oxide, boron oxide, molybdenum oxide and silicon oxide. Thus, in Example IX of the Table appearing on pages 12–13 of this '238 patent, the selectivity for acrylonitrile is indicated to be 35%, with a 32% propane conversion, but utilizing operating conditions whereunder the propane/ammonia/air reaction mixture (1/1.2/12) is in the explosive region.

French Patent No. 3,072,334 (corresponding to British Patent No. 1,336,135) describes a vapor phase process for the catalytic ammoxidation of alkanes at a temperature below 500° C. with a high concentration of alkane in the gaseous mixture feedstream, over a solid catalyst of tin oxide and molybdenum oxide (90/10 by weight); however, better results are attained using catalysts of antimony oxide and vanadium oxide.

French Patent No. 2,072,399 describes a process for the catalytic ammoxidation of alkanes, in vapor phase, employing a high concentration of alkane in the gaseous mixture feedstream, over a solid catalyst of, notably, a binary mixture of oxides, including molybdenum oxide.

The following pairs, or couples, are particularly representative:

(Mo, Sb) (Mo, Sn) (Mo, V) (Mo, Ti) (Mo, Bi).

However, none of these pairs performs better than those pairs which do not contain molybdenum. The acrylonitrile yields attained are very low; at best, 1.7% of the propane is converted into acrylonitrile at 570° C. on a catalyst based on tin and titanium oxides.

French Patent No. 2,119,492 (corresponding to U.S. Pat. No. 3,746,737 and to British Patent No. 1,337,759) describes utilizing a binary composition based on molybdenum and cerium oxides. However, the pair (Mo, Ce) performs insufficiently in the absence of halogen or of a halogen compound.

It is also suggested to add to this binary composition (Mo, Ce) a third element selected from tellurium and bismuth (cf. also U.S. Pat. No. 3,833,638). Again, however, the catalyst system appears to perform insufficiently in the absence of halogen or of a halogen compound. Moreover, it too will be appreciated that, in the presence of $CH_3Br$ the selectivity for acrylonitrile attains a value of 67% with 98% propane conversion, but under operating conditions which mandate a propane/ammonia/air reaction mixture (1/1.2/12) in the explosive region.

French Patent No. 2,119,493 also describes carrying out the vapor phase ammoxidation of alkanes over a solid catalyst containing bismuth and molybdenum oxides and, if appropriate, phosphorus and silica.

Here, too, the catalyst system appears to perform insufficiently in the absence of halogen or of a halogen compound, and the reaction mixture is again in the explosive region.

To obviate the aforesaid numerous shortcomings, various parallel or subsequent investigations have been conducted using solid catalysts based on vanadium and/or antimony.

Thus, *Chemistry Letters*, pp. 2173–2176 (1989) describes the vapor phase ammoxidation of propane, using multicomponent metal oxides containing molybdenum and bismuth and exhibiting a structure of the scheelite type. It would appear that, despite the relatively moderate temperatures used, the proportion of products of combustion ($CO$, $CO_2$) is very high in all instances (at least 15%) and that certain catalyst compositions display very little activity in respect of the desired reaction despite being employed under conditions wherein the reaction mixture is in the explosive region or very close to the such region.

The presence of a halogen compound likely will promote corrosion of the apparatus and is therefore not desirable on an industrial scale.

The coproduction of large amounts of $CO$ and of $CO_2$ is likewise undesirable on an industrial scale.

Lastly, the use of reaction mixtures which are compositionally within the explosive region is all the less desirable on an industrial scale because the process is carried out in a stationary bed.

SUMMARY OF THE INVENTION

Accordingly, a major object of the present invention is the provision of an improved process for the ammoxidation of alkanes exhibiting an appreciable selectivity for a mixture of final products that is commercially attractive, including an $\alpha,\beta$-unsaturated nitrile, in particular acrylonitrile, while at the same time reducing losses of raw material as a result of the formation of carbon oxides.

Another object of the invention is the provision of an improved such catalytic process in which the solid catalyst is relatively simple to prepare and active in the absence of a halogen-containing promoter, employing gaseous feedstream starting mixtures which, compositionally, are not necessarily in the explosive region.

Briefly, the present invention features a vapor phase process for the ammoxidation of alkanes in the presence of a catalytically effective amount of a solid catalyst, the active catalytic phase of which comprises molybdenum and oxygen, and, characteristically, also at least one element selected from among the alkaline earth metals, Mn, Fe, U, La, Co, Ni, Zn, Ag, Cd, W, Zr, Pb, Te, Ga, Al, B, Nb and Ta.

DETAILED DESCRIPTION OF THE PREFERRED EMBODIMENTS OF THE INVENTION

More particularly according to the present invention, acyclic saturated hydrocarbons having from 3 to 12 carbon atoms per molecule are reacted, in vapor phase, with ammonia and oxygen in the presence of a catalyst comprising an active phase as indicated immediately above.

It is within the scope of the present invention, of course, to employ diluent gases which are inert under the conditions of reaction, such as helium, nitrogen and argon. Similarly, water vapor can be included in the gaseous reaction mixture within wide limits. Thus, the reactive gas (saturated hydrocarbon, ammonia, oxygen) can be diluted with an inert diluent and/or with water vapor. Among such constituents, the water vapor content can vary over wide limits, in particular from 0% to 50% and preferably from 3% to 30%. In a preferred embodiment of the invention, the water vapor content in the reactive gas will be at least 3% and preferably at least 20%.

The respective amounts of saturated hydrocarbon, ammonia and oxygen comprising the reactive gas can also vary over wide limits.

The content of saturated hydrocarbon in the reactive gas preferably ranges from 5% to 70%. That of ammonia preferably ranges from 3% to 50% and that of oxygen preferably ranges from 3% to 45%.

BRIEF DESCRIPTION OF THE DRAWINGS

The process of the invention is advantageously carried out when the composition of the reactant mixture is outside the explosive region. In respect of the ammoxidation of propane in the absence of inert diluent, the composition (propane, oxygen, ammonia) of the starting admixture is preferably selected from within the quadrilateral ABDE indicated on the ternary diagram ABC shown in FIG. 1.

In this ternary diagram, the segment AB represents the ammonia content from 100% to 0%; the segment BC represents the propane content from 100% to 0%; the segment CA represents the oxygen content from 100% to 0%. The point D, situated inside the segment BC, corresponds to a propane content of 45%; in the binary (propane-$O_2$); the point E, situated inside the segment AC, corresponds to an ammonia content of 79% in the binary ($NH_3$-$O_2$).

The segment DE separates the ternary diagram into two parts: a triangle CDE within which the explosive region (determined at 1 bar and 25° C.) is situated and a quadrilateral ABDE, inside which the composition of the gaseous reactant mixture will advantageously be selected.

As regards the ammoxidation of propane in the presence of inert diluent gas(es) and/or of water vapor, it is appropriate to determine the composition of the ternary mixture (propane, oxygen and ammonia) in order to situate it in the aforesaid diagram, when the diluent gas and/or the water vapor is/are in a low proportion.

Figure 1:
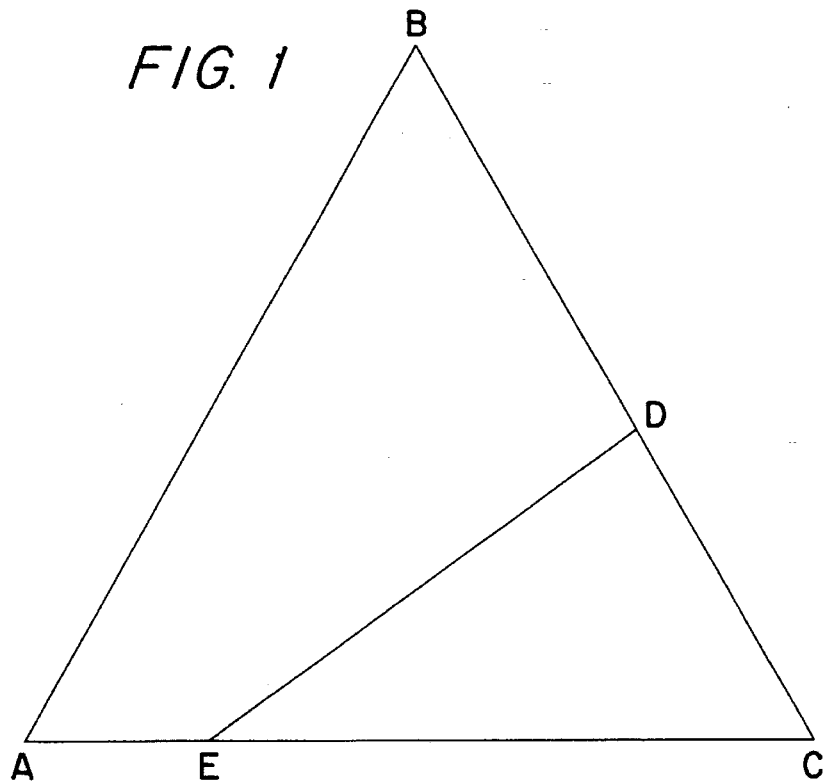
Figure 2:
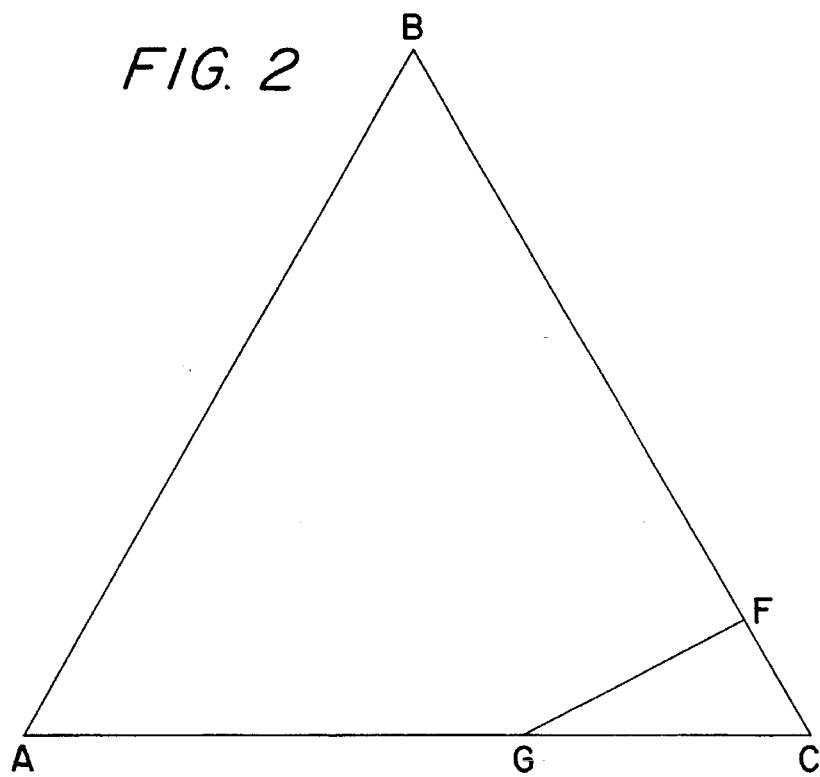

As regards the ammoxidation of propane using air as the source of oxygen, the composition (propane, air and ammonia) will advantageously be selected from within the quadrilateral ABFG indicated on the diagram ABC shown in FIG. 2.

In FIG. 2, the segment AB represents the ammonia content from 100% to 0%; the segment BC represents the propane content from 100% to 0%; the segment CA represents the air content from 100% to 0%. The point F, situated inside the segment BC, corresponds to a propane content of 16% in the binary (propane-air); the point G, situated inside segment AC, corresponds to an ammonia content of 35% in the binary (ammonia-air).

The segment FG separates the ternary diagram into two parts: a triangle CFG inside which the explosive region (determined at 1 bar and 500° C. ) is situated and a quadrilateral ABFG, inside which the composition of the gaseous reactant mixture will advantageously be selected.

This second diagram will be employed in the event that the oxygen/diluent gas mixture corresponds to an oxygen content equivalent to that of air ($\approx$21% of oxygen) or in the event that this mixture is oxygen-deficient relative to air.

A mixture principally containing propylene and acrylonitrile will be obtained when using propane as a starting material. Acrylonitrile is an intermediate which is produced industrially on a vast scale; propylene is a raw material conventionally employed for producing acrylonitrile and various other intermediates which are well known to this art.

A mixture containing methacrylonitrile and isobutene or n-butenes will be prepared from an isobutane starting material.

The process according to the invention is more particularly well suited for the ammoxidation of propane.

While the saturated hydrocarbon starting material may be of technical grade, it will not contain appreciable amounts of ethylenically unsaturated compounds. Thus, the propane starting material will contain propylene only in trace quantities.

The process according to the invention is carried out in the vapor phase. Any suitable apparatus for conducting vapor phase ammoxidation or oxidation reactions can consequently be employed. The process can be carried out continuously or noncontinuously and may entail the use of a stationary bed or of a fluidized bed.

The reaction temperature typically ranges from 350° to 550° C. and preferably from 420° to 510° C.

The total pressure of the reaction mixture may be higher than or equal to atmospheric pressure. It typically ranges from 1 to 6 bar and preferably from 1 to 4 bar.

The gas flowrate is advantageously adjusted such that the hourly space velocity ranges from 100 to 36,000 $h^{-1}$ and preferably from 200 to 20,000 $h^{-1}$.

One skilled in this art will, of course, determine a suitable compromise among the temperature, the gas flowrate, the precise nature of the catalyst used and the various other reaction parameters, bearing in mind his production objectives.

In the process according to the present invention, a solid catalyst is used whose active phase contains molybdenum and oxygen, said active phase necessarily also comprising at least one element selected from among the alkaline earth metals, Mn, Fe, U, La, Co, Ni, Zn, Ag, Cd, W, Zr, Pb, Te, Ga, Al, B, Nb and Ta.

The active catalytic phases, one of the constituents of the catalyst employed in the present invention, comprise molybdenum-based mixed oxides which preferably contain at least two elements selected from among those indicated above. Good results are attained using such an active phase containing at least one element selected from among the alkaline earth metals, manganese, iron, cobalt, uranium and lanthanum.

The subject active catalytic phases are preferably molybdates. The more preferred active phases comprise manganese, uranyl, cobalt or iron molybdates.

While the proportion of element(s) M selected from among those indicated above can vary over wide limits in the subject active phases, the minimum will preferably be indicated by the stoichiometry of formation of the corresponding orthomolybdate. In certain instances and depending on the nature of M, a mixture of the corresponding molybdate and of a molydenum oxide will be obtained by decreasing the proportion of element(s) M.

Thus, for example, a large excess of molybdenum in relation to iron (Mo/Fe=10) results in the formation of a mixture of $Fe_2(MoO_4)_3$ and of $MoO_3$, the performance of which in the process of the invention is less attractive than that obtained with $Fe_2(MoO_4)_3$.

The above active catalytic phases can be present in bulk form or in the particulate state. These phases can be employed in the form of powders or beads, which are, for example, extruded or crushed.

They can also be deposited onto an inert support or as a coating therefor. The nature of the support is not critical, provided that its is chemically inert towards the reactants under the reaction conditions selected. Exemplary such supports suitable for the preparation of catalysts according to the invention include silica, alumina, silica alumina, sintered clay, carborundum, magnesia, magnesium silicate and diatomaceous earth. The support is preferably nonporous and may be, in particular, based on a refractory oxide in particulate form, the most commonly employed support being clay-based. This support may, for example, comprise inert, solid and coarse clay beads having a diameter ranging from 0.5 to 6 mm. The precise value of the diameter of the beads will be selected by one skilled in this art as a function of the pressure drop which is permissible in the reactor. The support may also be rendered nonporous by enamelling.

The support may also be a ceramic substrate, such substrate preferably being in the form of an inert and rigid structure of monolithic type comprising channels or conduits. Such supports are well known to this art and have been widely described in the literature. Exemplary such substrates include, in particular, those based on cordierite, alumina, mullite, porcelain and boron or silicon carbides.

When a coated catalyst is appropriate, the amount of active phase, which may vary over wide limits, ranges from 5% to 35% as a practical matter and preferably from 10% to 15% by weight relative to the total weight of the catalyst (support+active phase).

The preparation of the catalysts used in the process according to the invention is essentially conventional, and entails, for example, mixing appropriate salts of the elemental constituents in water or in another solvent, followed by evaporation to dryness, or by precipitation by means of a base such a aqueous ammonia or an acid such as hydrochloric acid, or by spraying a suspension obtained after mixing suitable salts.

The suitable salts most typically employed are soluble in water and contain anions and cations which can be decomposed by heating during subsequent stages. They include, for example, ammonium heptamolybdate in the case of molybdenum, and alkaline earth metal, manganese, iron, cobalt, uranium, lanthanum, etc., nitrates or chlorides in the case of metals.

Once the mixture of the salts has been provided, a precursor can be obtained by the so-called evaporation method. The water in the resulting suspension is evaporated off by heating to a temperature of from 20° to 100° C. with stirring for the period of time required to obtain a paste which does not run. Stirring and heating are then stopped.

The paste thus obtained, spread out into a thickness of approximately 2 cm, is dried in air at approximately 120° C. for approximately 15 h. The precursor thus prepared can then be ground and calcined at a temperature of from 200° to 1,000° C., preferably from 400° to 600° C. for at least 30 min, preferably at least one hour. The calcination may be carried out by progressively increasing the temperature, for example 100° to 200° C. per hour, in particular taking account of the risks associated with the exothermic decomposition of ammonium nitrate at about 230° C. The active phase thus obtained after cooling can then be ground in order that its particle size should not exceed approximately 400 µm.

The precursor can also be obtained by an alternative method comprising precipitation by means of the addition, for example, of aqueous ammonia or of hydrochloric acid upon completion of mixing of the salts, to stabilize the pH at approximately 7. It is preferable to heat the suspension at a temperature of from 20° to 100° C. for approximately one hour to complete the precipitation of the species.

The suspension is then filtered and washed. The filter cake is next spread out and then dried, ground and calcined under the conditions described above.

Certain catalysts which are useful for conducting the subject process in a stationary bed can be obtained by coating onto appropriate substrate, in a manner know per se, of ground, intermediate or final product active catalytic phases. This traditional technique entails depositing a layer of intermediate or finished active phase around inert but coarse beads.

Once the beads are coated with the intended amount of the active phase, they are dried using hot air, at a temperature of from 70° to 150° C. for at least 30 minutes, and are then calcined in an oven at a temperature of from 300° to 600° C., preferably from 450° to 500° C., for at least 3 hours.

And certain catalysts for conducting the process according to the invention in a stationary bed or fluidized bed can be obtained by the technique, also per se known to this art, of spray-drying in a preferably nonreducing atmosphere. In accordance with such technique, if appropriate followed by a calcination at a temperature on the order of 400° to 1,100° C., powders of spherical form having a diameter ranging from 5 to 700 µm are obtained. Powders which comprise at least 80% by weight of particles which range from 5 to 100 µm in size are preferred for fluidized bed applications.

The reaction products can be recovered from the effluent gases by any appropriate means. For example, the effluent gases may be directed through a condenser containing dilute sulfuric acid to neutralize the unconverted ammonia. The gases may then be transported through a refrigerated absorbing column to condense the acrylonitrile, acetonitrile and hydrocyanic acid, the uncondensed vapor containing, principally, unconverted propane, propylene, light hydrocarbons and, where applicable, $CO_2$. Acrylonitrile and hydrocyanic acid can then be separated from the acetonitrile by distillation and the recovered acrylonitrile/hydrocyanic acid mixture can then itself be distilled to separate the acrylonitrile from the hydrocyanic acid.

In order to further illustrate the present invention and the advantages thereof, the following specific examples are given, it being understood that same are intended only as illustrative and in nowise limitative.

EXAMPLE 1

Preparation Of A Catalyst Based On Magnesium Molybdate

A solution (a) of ammonium heptamolybdate was prepared by dissolving 52.98 g of $(NH_4)_6Mo_7O_{24} \cdot 4H_2O$ (marketed by Merck) in 200 cm³ of demineralized water (pH of the solution obtained: 5–6), and a solution (b) of magnesium nitrate by dissolving 79.3 g of 97% $Mg(NO_3)_2 \cdot 6H_2O$ (marketed by Prolabo) in 200 cm³ of demineralized water. The solution (b) was added to the solution (a) in a stirred reactor (pH=5). The mixture was heated on a hotplate and the resulting paste was dried at 120° C. for approximately 15 h; the product obtained was then ground in a mortar and calcined in air at 500° C. for 4 h.

The product (I) thus prepared had the composition $MgMoO_4$, identified by X-ray diffraction, and had a specific surface, measured by the B.E.T. method, of 5 $m^2g^{-1}$.

20 g of the product (I) were slowly sprinkled onto 123 g of inert support, i.e., clay beads having a mean diameter of 4.8 mm, preliminarily heated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) had been coated onto the beads. Drying was then carried out at 120° C. for 2 h and calcining at 480° for 6 h.

The catalyst (A) thus prepared contained 12% by weight of $MgMoO_4$ deposited onto the clay beads.

EXAMPLE 2

Preparation Of A Catalyst Based On Manganese Molybdate

An active catalytic phase of composition $MnMoO_4$ was prepared following the operating procedure described by U. Ozran, R. C. Gill and M. R. Smith, *J. Catal.*, 116, 171–183 (1989).

A solution (a) of ammonium heptamolybdate was prepared by dissolving 70.64 g of $(NH_4)_6Mo_7O_{24} \cdot 4H_2O$ (marketed by Merck) in 200 cm³ of demineralized water, and a solution (b) of manganese chloride by dissolving 79.16 g of $MnCl_2 \cdot 4H_2O$ (marketed by Prolabo) in 400 cm³ of demineralized water. The solution (a) was added dropwise to the solution (b) in a vigorously stirred reactor. The mixture was heated to 80° C. and the pH was maintained at 6 by adding dilute hydrochloric acid or aqueous ammonia (both marketed by Prolabo) for 3 h. The material was filtered hot on sintered glass and washed with 1 l of demineralized water. The product obtained was then dried at 120° C. for approximately 15 h, ground in a mortar, and calcined in air at 500° C. for 4 h.

The product (I) thus prepared had the composition $MnMoO_4$, identified by X-ray diffraction, and had a specific surface, measured by the B.E.T. method, of 5 $m^2 g^{-1}$.

20 g of the product (I) were sprinkled slowly onto 123 g of inert support, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed therefor. The product (I) was then again sprinkled onto the beads. These operations were continued alternately until all of the product (I) had been coated onto the beads. Drying was then carried out at 120° C. for 2 h and calcining at 480° C. for 6 h.

The catalyst (B) thus prepared contained 11% by weight of $MnMoO_4$ deposited onto the clay beads.

EXAMPLE 3

Preparation Of Another Catalyst Based On Manganese Molybdate 20 g of product (I) of composition $MnMoO_4$ as described in the preceding example were prepared. This product was then compressed under a pressure of 20 t. Tablets 3 cm in diameter and approximately 0.5 cm in thickness were thus obtained. These tablets were then crushed into fragments having a particle size ranging from 0.3 to 0.8 cm, constituting the catalyst (C).

EXAMPLE 4

Preparation Of A Catalyst Based On Uranyl Molybdate

An active catalytic phase of composition $UO_2MoO_4$ was prepared by following the operating procedure described by E. Bordes, *State Thesis*, Compiegne, France (1979).

A solution (a) of ammonium heptamolybdate was prepared by dissolving 35.32 g of $(NH_4)_6Mo_7O_{24}4 \cdot H_2O$ (marketed by Merck) in 200 cm³ of demineralized water, and a solution (b) of uranyl nitrate by dissolving 100.43 g of $UO_2(NO_3)_2 \cdot 6H_2O$ (marketed by Prolabo) in 200 cm³ of demineralized water. The solution (b) was added to the solution (a) in a stirred reactor. 100 cm³ of demineralized water were added, the mixture was heated on a hotplate and the resulting paste was dried at 120° C. for approximately 15 h; the product obtained was then ground in a mortar and calcined in air at 550° C. for 12 h.

The product (I) thus prepared had the composition $UO_2MoO_4$, identified by X-ray diffraction, and had a specific surface, measured by the B.E.T. method, of 2.7 $m^2 g^{-1}$.

20 g of the product (I) were sprinkled slowly onto 123 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) had been coated. Drying was then carried out at 120° C. for 2 h and calcining at 480° C. for 6 h.

The catalyst (D) thus prepared contained 11% by weight of $UO_2MoO_4$ deposited onto the clay beads.

EXAMPLE 5

Preparation Of A Catalyst Based On Calcium Molybdate

A solution (a) of ammonium heptamolybdate was prepared by dissolving 52.89 g of $(NH_4)_6Mo_7O_{24} \cdot 4H_2O$ (marketed by Merck) in 200 cm³ of demineralized water, and a solution (b) of calcium nitrate by dissolving 47.23 g of $Ca(NO_3)_2 \cdot 4H_2O$ (marketed by Prolabo) in 200 cm³ of demineralized water. The solution (b) was added to the solution (a) in a stirred reactor. The pH of the mixture, initially 4.5, was increased to 6.7 by adding aqueous ammonia (marketed by Prolabo). Heating was carried out on a hotplate and the resulting paste was dried at 120° C. for approximately 15 h; the product obtained was then ground in a mortar and calcined in air at 500° C. for 7 h.

The product (I) thus prepared had the composition $CaMoO_4$, identified by X-ray diffraction, and had a specific surface, measured by the B.E.T. method, of 5 m$^2$ g$^{-1}$.

20 g of the product (I) were sprinkled slowly on to 123 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) had been coated. Drying was then carried out at 120° C. for 2 h and calcining at 480° C. for 6 h.

The catalyst (E) thus prepared contained 11% by weight of $CaMoO_4$ deposited onto the clay beads.

EXAMPLE 6

Preparation Of A Catalyst Based On Mixed Molybdenum/Lanthanum Oxide

A solution (a) of ammonium heptamolybdate was prepared by dissolving 35.32 g of $(NH_4)_6Mo_7O_{24} \cdot 4H_2O$ (marketed by Merck) in 200 cm$^3$ of demineralized water, and a solution (b) of lanthanum nitrate by diluting 71.64 cm$^3$ of $La(NO_3)_3$ containing 455 g l$^{-1}$ a $La_2O_3$ (source: Rhone-Poulenc plant in La Rochelle, France) in 200 cm$^3$ of demineralized water. The solution (a) was added to the solution (b) in a stirred reactor. The mixture was acidified to pH=1–2 by adding concentrated nitric acid. Heating was carried out on a hotplate at 100°–110° C. and the resulting paste was dried at 120° C. for approximately 15 h; the product obtained was then ground in a mortar and calcined in air at 500° C. for 3 h.

The product (I) thus prepared contained a mixture of lanthanum and molybdenum oxides, identified by X-ray diffraction, and had a specific surface, measured by the B.E.T. method, of 6 m$^2$ g$^{-1}$.

20 g of the product (I) were sprinkled slowly onto 123 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) was coated. Drying was then carried out at 120° C. for 2 h and calcining at 480° C. for 6 h.

The catalyst (F) thus prepared contained 9% by weight of $LaMoO_x$ deposited onto the clay beads.

EXAMPLE 7

Preparation Of A Catalyst Based On Iron Molybdate

An active phase of composition $Fe_2(MoO_4)_3$ was prepared by following the operating procedure described by S. Nasu and S. Shimizu, *J. Catal.*, 104, 164–175 (1987).

A solution (a) of ammonium heptamolybdate was prepared by dissolving 52.98 g of $(NH_4)_6Mo_7O_{24} \cdot 4H_2O$ (marketed by Merck) in 200 cm$^3$ of demineralized water, and a solution (b) of iron nitrate by dissolving 80.8 g of $Fe(NO_3)_3 \cdot 9H_2O$ (marketed by Prolabo) in 200 cm$^3$ of demineralized water. The solution (b) was added to the solution (a) in a stirred reactor. The pH of the mixture was adjusted to 7.5 by adding aqueous ammonia (marketed by Prolabo). The mixture was heated on a hotplate and the resulting paste was dried at 120° C. for approximately 15 h; the product obtained was then ground in a mortar and calcined in air at 500° C. for 1 h and reground and recalcined in air at 500° C. for 1 hr.

The product (I) thus prepared had the composition $Fe_2(MoO_4)_3$, identified by X-ray diffraction, and had a specific surface, measured by the B.E.T. method, of 3.9 m$^2$ g$^{-1}$.

20 g of the product (I) were sprinkled slowly onto 123 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) was coated. Drying was then carried out at 120° C. for 2 h and calcining at 480° C. for 6 h.

The catalyst (G) thus prepared contained 13% by weight of $Fe_2(MoO_4)_3$ deposited onto the clay beads.

EXAMPLE 8

Preparation Of A Control Catalyst Based On Mixed Molybdenum/Tin Oxide (This catalyst is not according to the invention).

A solution (a) of ammonium heptamolybdate was prepared by dissolving 35.32 g of $(NH_4)_6Mo_7O_{24} \cdot 4H_2O$ (marketed by Merck) in 200 cm$^3$ of demineralized water, and a solution (b) of tin chloride by dissolving 45.13 g of $SnCl_2 \cdot 2H_2O$ (marketed by Prolabo) in 200 cm$^3$ of demineralized water, acidified with a few drops of concentrated hydrochloric acid. The solution (b) was added to the solution (a) in a stirred reactor. The mixture was heated and aqueous ammonia (marketed by Prolabo) was added to neutral pH. The material was filtered on sintered glass and washed with 100 cm$^3$ of demineralized water; the product obtained was dried at 120° C. for approximately 15 h, ground in a mortar and calcined in air at 500° C. for 3 h.

The product (I) thus prepared had the composition $SnO_2 \cdot 2MoO_3$, identified by x-ray diffraction, and had a specific surface, measured by the B.E.T. method, of 26 m$^2$ g$^{-1}$.

20 g of the product (I) were sprinkled slowly onto 123 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) was coated. Drying was then carried out at 120° C. for 2 h and calcining at 480° C. for 6 h.

The catalyst (H) thus prepared contained 11% by weight of $SnO_2 \cdot 2MoO_3$ deposited onto the clay beads.

EXAMPLE 9

Preparation Of A Catalyst Based On Manganese Molybdate And Alumina (30–70% wt)

A solution (a) was prepared by dissolving 26.47 g of $(NH_4)_6Mo_7O_{24}\cdot 4H_2O$ in 120 cm$^3$ of demineralized water, and a solution (b) by dissolving 37.65 g of $Mn(NO_3)_2\cdot 4H_2O$ in 60 cm$^3$ of demineralized water and a suspension (c) of 75.2 of alumina in 100 cm$^3$ of demineralized water. The solution (a) was added to the solution (c) and the solution (b) was then added. Stirring was carried out for 2 h and the material was evaporated to dryness. It was then dried at 120° C. and calcined at 500° C. for 4 h. A product (I) was thus obtained.

20 g of the product (I) were sprinkled slowly onto 123 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product (I) was then again sprinkled onto the beads. These operations were continued alternately until all of the product (I) was coated.

Drying was then carried out at 120° C. for 2 h and calcining at 480° C. for 6 h. The catalyst (J) thus prepared contained 11% by weight of $MnMoO_4$-$Al_2O_3$ (30–70 wt %) deposited onto the clay beads.

EXAMPLE 10

Preparation Of A Catalyst Based On Manganese Molybdate And Silica

A solution (a) was prepared by dissolving 58.3 g of $(NH_4)_2Mo_2O_7$ and 8.2 g of $MoO_3$ in 150 cm$^3$ of demineralized water at 50°–60° C. A solution (b) was prepared by dissolving 100.4 g of $Mn(NO_3)_2\cdot 4H_2O$ in 100 cm$^3$ of demineralized water. The solution (b) was added to the solution (a) at room temperature.

31.9 cm$^3$ adjusted to 40 cm$^3$ of the solution obtained were then impregnated dry onto 50 g of silica beads. Drying was then carried out at 120° C. for approximately 15 h and calcining at 500° C. for 4 h.

The catalyst (K) thus prepared contained 14.6% by weight of $MnMoO_4$ deposited onto the silica beads.

General Operating Procedure For The Ammoxidation Tests

The catalyst sample was preheated on a measuring bench to a temperature of 150° C. under helium blanketing for 10 min and was then subjected to a gas flow whose composition will be indicated for each example and which contained propane, ammonia, oxygen, water vapor and helium.

The total pressure of the reaction mixture, ranging from 1 to 6 bar, will also be indicated for each example.

The gas flowrate was determined such as to provide an hourly space velocity (HSV) ranging from 100 to 36,000 h$^{-1}$ the precise value of which will also be indicated for each example.

The principle of the propane ammoxidation test was the following:

(a) The catalyst was heated to a temperature $T_1$, for example 300° C., and after 30 min of stabilization at the temperature $T_1$ the composition of the mixture exiting the reactor was determined by gas phase chromatography;

(b) The percentages of conversion and the selectivities obtained with the catalyst examined at the inlet temperature $T_1$ were calculated using relationships of the type:

Propane conversion=% propane converted/% propane introduced Selectivity for acrylonitrile=% propane converted into acrylonitrile/% propane converted;

(c) The catalyst was then heated from 300° to 550° C. in 20° C. increments and the percentages of conversion and the selectivities were determined every 40 min.

The following conventions are employed in the examples below:

DCC3H8=propane conversion

SACN=selectivity for acrylonitrile

SACN+$C_3H_6$=selectivity for acrylonitrile and propylene

SCOX=selectivity for carbon monoxide and dioxide.

EXAMPLES 11 TO 13

Measurement of the performance of catalysts (A), (B) and (D):

The operating conditions employed were the following:

Hourly space velocity=1,000 h$^{-1}$

Total pressure=1.3 bar

Composition of the reaction mixture:

$C_3H_8$=11%

$NH_3$=7.5 %

$O_2$=10%

$H_2O$=25%

He=46.5%

The results and the particular conditions employed are reported in Table I below:

TABLE I

| EXAMPLE | CATALYST | T° C. | DCC$_3$H$_8$ (%) | SACN (%) | SACN + C$_3$H$_6$ (%) | SCOX (%) |
|---|---|---|---|---|---|---|
| 11 | (A) | 470 | 6 | 10 | 73 | 0 |
| 12 | (B) | 470 | 2 | 1 | 98 | 0 |
|  |  | 510 | 5.5 | 19 | 77 | 0 |
| 13 | (D) | 470 | 3 | 15 | 44 | 0 |
|  |  | 510 | 5 | 14 | 71 | 0 |

EXAMPLE 14 TO 16

Control Test a

Measurement of the performance of catalysts (E) to (H):

The operating conditions employed were the following:

Hourly space velocity 1,000 h$^{-1}$

Total pressure=1.3 bar

Composition of the reaction mixture:

$C_3H_8$=30%

$NH_3$=15%

$O_2$=15%

$H_2O$=20%

He=20%

The results and the particular conditions employed are reported in Table II below:

TABLE II

| EXAMPLE | CATALYST | T° C. | DCC$_3$H$_8$ (%) | SACN (%) | SACN + C$_3$H$_6$ (%) | SCOX (%) |
|---|---|---|---|---|---|---|
| 14 | (E) | 475 | 2 | 0 | 78 | 0 |
|  |  | 490 | 4 | 9.5 | 69 | 0 |
| 15 | (F) | 460 | 1 | 3 | 83 | 0 |
|  |  | 490 | 7 | 19 | 55 | 0 |
|  |  | 510 | 7.5 | 10 | 60 | 6 |
| 16 | (G) | 460 | 5 | 20 | 59 | 0 |
|  |  | 475 | 7 | 23 | 56 | 0 |
|  |  | 490 | 6 | 19 | 58 | 13 |
| a | (H) | 440 | 9 | 6 | 32 | 19 |

TABLE II-continued

| EX-AMPLE | CATA-LYST | T° C. | $DCC_3H_8$ (%) | SACN (%) | SACN + $C_3H_6$ (%) | SCOX (%) |
|---|---|---|---|---|---|---|
| | | 460 | 11 | 20 | 43 | 16 |
| | | 475 | 11 | 24 | 47 | 13 |

EXAMPLES 17 TO 19

Measurement of the performance of catalyst (A) at different partial pressure of propane:

The operating conditions employed were the following:
Temperature=510° C.
1,000 h$^{-1}$
Hourly space velocity=
Total pressure=1.3 bar
Composition of the reaction mixture:
  $C_3H_8$=11% or 19 or 26%
  $NH_3$=7.5%
  $O_2$=10%
  $H_2O$ =25%
  He=31.5% or 38.5 or 46.5%

The results and the particular conditions employed are reported in Table III below:

TABLE III

| EXAMPLE | $C_3H_8$ (%) | $DCC_3H_8$ (%) | SACN (%) | SACN + $C_3H_6$ (%) | SCOX (%) |
|---|---|---|---|---|---|
| 17 | 11 | 17 | 3 | 50 | 21 |
| 18 | 19 | 16 | 16 | 69 | 5 |
| 19 | 26 | 16 | 13 | 72 | 5.5 |

EXAMPLES 20 TO 23

Measurement of the performance of catalyst (B) at different temperatures:

The operating conditions employed were the following:
Hourly space velocity=1,000 h$^{-1}$
Total pressure=1.3 bar
Composition of the reaction mixture:
  $C_3H_8$=19%
  $NH_3$=7.5%
  $O_2$=10%
  $H_2O$=25%
  He=38.5%

The results and the particular conditions employed are reported in Table IV below:

TABLE IV

| EXAMPLE | T° C. | $DCC_3H_8$ (%) | SACN (%) | SACN + $C_3H_6$ (%) | SCOX (%) |
|---|---|---|---|---|---|
| 20 | 420 | 0.4 | 16 | 81 | 0 |
| 21 | 470 | 2 | 17 | 72 | 0 |
| 22 | 485 | 3 | 17 | 71 | 0 |
| 23 | 510 | 8 | 30 | 67 | 0 |

EXAMPLES 24 TO 26

Measurement of the performance of catalyst (B) at different hourly space velocities:

The operating conditions employed were the following:
Temperature=510° C.
Total pressure=1.3 bar
Composition of the reaction mixture:
  $C_3H_8$=19%
  $NH_3$=7.5%
  $O_2$=10%
  $H_2O$=25%
  He=38.5%

The particular conditions employed and the results obtained are reported in Table V below:

TABLE V

| EX-AMPLE | HSV (h$^{-1}$) | Cat. Vol. (ml) | $DCC_3H_8$ (%) | SACN (%) | SACN + $C_3H_6$ (%) | SCOX (%) |
|---|---|---|---|---|---|---|
| 24 | 200 | 100 | 13 | 21 | 77 | 2 |
| 25 | 500 | 40 | 13 | 27 | 65 | 0 |
| 26 | 1,000 | 20 | 8 | 30 | 67 | 0 |

EXAMPLES 27 TO 31

Measurement of the performance of catalyst (B) at different temperatures:

The operating conditions employed were the following:
Hourly space velocity=500 h$^{-1}$
Total pressure=1.3 bar
Composition of the reaction mixture:
  $C_3H_8$=19%
  $NH_3$=7.5%
  $O_2$=10%
  $H_2O$=25%
  He=38.5%

The results and the particular conditions employed are reported in Table VI below:

TABLE VI

| EXAMPLE | T° C. | $DCC_3H_8$ (%) | SACN (%) | SACN + $C_3H_6$ (%) | SCOX (%) |
|---|---|---|---|---|---|
| 27 | 420 | 1 | 3 | 87 | 0 |
| 28 | 450 | 3 | 15 | 58 | 0 |
| 29 | 470 | 5 | 20 | 62 | 0 |
| 30 | 490 | 9 | 27 | 62 | 0 |
| 31 | 510 | 13 | 27 | 65 | 0 |

EXAMPLES 32 TO 36

Measurement of the performance of catalyst (C) at different temperatures:

The operating conditions employed were the following:
Hourly space velocity 1,000 h$^{-1}$
Total pressure=1.3 bar
Composition of the reaction mixture:
  $C_3H_8$=19%
  $NH_3$=7.5%
  $O_2$=10%
  $H_2O$=25%
  He=38.5%

The particular conditions employed and the results obtained are reported in Table VII below:

TABLE VII

| EXAMPLE | T° C. | DCC$_3$H$_8$ (%) | SACN (%) | SACN + C$_3$H$_6$ (%) | SCOX (%) |
|---|---|---|---|---|---|
| 32 | 410 | 3 | 9 | 64 | 0 |
| 33 | 430 | 6 | 13 | 74 | 0 |
| 34 | 470 | 11 | 16 | 76 | 4 |
| 35 | 490 | 20 | 23 | 73 | 9 |
| 36 | 510 | 24 | 24 | 73 | 6 |

EXAMPLES 37 TO 39

Measurement of the performance of catalyst (B) at different partial pressures of propane:

The operating conditions employed were the following:
Temperature=510° C.
Hourly space velocity 1,000 h$^{-1}$
Total pressure=1.3 bar
Composition of the reaction mixture:
  C$_3$H$_8$=11% or 19 or 26%
  NH$_3$=7.5%
  O$_2$=10%
  H$_2$O=25%
  He=31.5% or 38.5 or 46.5%

The particular conditions employed and the results obtained are reported in Table VIII below:

TABLE VIII

| EXAMPLE | C$_3$H$_8$ (%) | DCC$_3$H$_8$ (%) | SACN (%) | SACN + C$_3$H$_6$ (%) | SCOX (%) |
|---|---|---|---|---|---|
| 37 | 11 | 5 | 19 | 77 | 0 |
| 38 | 19 | 8 | 30 | 67 | 0 |
| 39 | 26 | 5 | 13 | 80 | 0 |

EXAMPLES 40 TO 42

Measurement of the performance of catalyst (B) at different partial pressures of ammonia:

The operating conditions employed were the following:
Temperature=510° C.
Hourly space velocity 1,000 h$^{-1}$
Total pressure=1.3 bar
Composition of the reaction mixture:
  C$_3$H$_8$=19%
  NH$_3$=4% or 7.5 or 11%
  O$_2$=10%
  H$_2$O=25%
  He=35% or 38.5 or 42%

The particular conditions employed and the results obtained are reported in Table IX below:

TABLE IX

| EXAMPLE | NH$_3$ (%) | DCC$_3$H$_8$ (%) | SACN (%) | SACN + C$_3$H$_6$ (%) | SCOX (%) |
|---|---|---|---|---|---|
| 40 | 4 | 4 | 0 | 82 | 17 |
| 41 | 7.5 | 8 | 30 | 67 | 0 |
| 42 | 11 | 10 | 30 | 60 | 0 |

EXAMPLES 43 TO 45

Measurement of the performance of catalyst (D) at different partial pressures of propane:

The operating conditions employed were the following:
Temperature=510° C.
Hourly space velocity=1,000 h$^{-1}$
Total pressure=1.3 bar
Composition of the reaction mixture:
  C$_3$H$_8$=11% or 19 or 26%
  NH$_3$=7.5%
  O$_2$=10%
  H$_2$O=25%
  He=31.5% or 38.5 or 46.5%

The particular conditions employed and the results obtained are reported in Table X below:

TABLE X

| EXAMPLE | C$_3$H$_8$ (%) | DCC$_3$H$_8$ (%) | SACN (%) | SACN + C$_3$H$_6$ (%) | SCOX (%) |
|---|---|---|---|---|---|
| 43 | 11 | 5 | 14 | 71 | 0 |
| 44 | 19 | 4 | 11 | 73 | 0 |
| 45 | 26 | 7 | 22 | 54 | 0 |

EXAMPLES 46 TO 48

Measurement of the performance of catalyst (D) at different partial pressures of ammonia:

The operating conditions employed were the following:
Temperature=510° C.
Hourly space velocity=1,000 h$^{-1}$
Total pressure=1.3 bar
Composition of the reaction mixture:
  C$_3$H$_8$=19%
  NH$_3$=4% or 7.5 or 11%
  O$_2$=10%
  H$_2$O=25%
  He=35% or 38.5 or 42%

The particular conditions employed and the results obtained are reported in Table XI below:

TABLE XI

| EXAMPLE | NH$_3$ (%) | DCC$_3$H$_8$ (%) | SACN (%) | SACN + C$_3$H$_6$ (%) | SCOX (%) |
|---|---|---|---|---|---|
| 46 | 4 | 6 | 24 | 62 | 0 |
| 47 | 7.5 | 4 | 11 | 73 | 0 |
| 48 | 11 | 4 | 13 | 70 | 0 |

EXAMPLES 49 TO 51

Measurement of the performance of catalyst (F) at different partial pressures of oxygen:

The operating conditions employed were the following:
Temperature=490° C.
Hourly space velocity 1,000 h$^{-1}$
Total pressure=1.3 bar
Composition of the reaction mixture:
  C$_3$H$_8$=20%
  NH$_3$=15%
  O$_2$=5% or 15 or 25%
  H$_2$O=20%
  He=20% or 30 or 40%

The particular conditions employed and the results obtained are reported in Table XII below:

TABLE XII

| EXAMPLE | $O_2$ (%) | $DCC_3H_8$ (%) | SACN (%) | SACN + $C_3H_6$ (%) | SCOX (%) |
|---|---|---|---|---|---|
| 49 | 5 | 4 | 15 | 63 | 0 |
| 50 | 15 | 6 | 14 | 59 | 0 |
| 51 | 25 | 8 | 18 | 58 | 4 |

EXAMPLES 52 AND 53

Measurement of the performance of catalyst (G) at different partial pressures of ammonia:

The operating conditions employed were the following:
Temperature=490° C.
Hourly space velocity 1,000 h$^{-1}$
Total pressure=1.3 bar
Composition of the reaction mixture:
  $C_3H_8$=20%
  $NH_3$=5% or 25%
  $O_2$=5%
  $H_2O$=20%
  He=20% or 40%

The particular conditions employed and the results obtained are reported in Table XIII below:

TABLE XIII

| EXAMPLE | $NH_3$ (%) | $DCC_3H_8$ (%) | SACN (%) | SCAN + $C_3H_6$ (%) | SCOX (%) |
|---|---|---|---|---|---|
| 52 | 5 | 12 | 17 | 45 | 28 |
| 53 | 25 | 14 | 7 | 42 | 4 |

EXAMPLES 54 AND 55

Measurement of the performance of catalyst (G) at different partial pressures of oxygen:

The operating conditions employed were the following:
Temperature=475° C.
Hourly space velocity 1,000 h$^{-1}$
Total pressure=1.3 bar
Composition of the reaction mixture:
  $C_3H_8$=20%
  $NH_3$=15%
  $O_2$=5% or 25%
  $H_2O$=20%
  He=20% or 40%

The particular conditions employed and the results obtained are reported in Table XIV below:

TABLE XIV

| EXAMPLE | $O_2$ (%) | $DCC_3H_8$ (%) | SACN (%) | SACN $C_3H_6$ (%) | SCOX |
|---|---|---|---|---|---|
| 54 | 5 | 8 | 15 | 58 | 4 |
| 55 | 25 | 11 | 17 | 60 | 14 |

EXAMPLES 56 AND 57

Measurement of the performance of catalysts (J) and (K):
The operating conditions employed were the following:
Hourly space velocity 1,000 h$^{-1}$
Total pressure=1.3 bar
Composition of the reaction mixture:
  $C_3H_8$=48%
  $NH_3$=95%
  $O_2$=18%
  $H_2O$=20%
  He=5%

The particular conditions employed and the results obtained are reported in Table XV below:

TABLE XV

| EXAMPLE | CATALYST | T° C. | $DCC_3H_8$ (%) | SACN (%) | SACN + $C_3H_6$ (%) | SCOX (%) |
|---|---|---|---|---|---|---|
| 56 | (J) | 500 | 15 | 15 | 62 | 0 |
| 57 | (K) | 460 | 12 | 14 | 37 | 0.2 |

Control tests b, c, d

Measurement of the performance of catalyst (H) at different temperatures:

The operating conditions employed were the following:
Hourly space velocity 1,000 h$^{-1}$
Total pressure=1.3 bar
Composition of the reaction mixture:
  $C_3H_8$=20%
  $NH_3$=5%
  $O_2$=15%
  $H_2O$=20%
  He=40%

The particular conditions employed and the results obtained are reported in Table XVI below:

TABLE XVI

| EXAMPLE | T° C. (%) | $DCC_3H_8$ (%) | SACN (%) | SACN + $C_3H_6$ (%) | SCOX (%) |
|---|---|---|---|---|---|
| b | 460 | 19 | 13 | 25 | 38 |
| c | 475 | 20 | 19 | 32 | 43 |
| d | 490 | 21 | 26 | 41 | 28 |

EXAMPLE 58

Preparation Of A Catalyst Based On Uranyl Molybdate

An active catalytic phase of composition $UMo_{10}O_x$ was prepared according to the following operating procedure:

A solution (a) of ammonium heptamolybdate was prepared by dissolving 176.56 g of $(NH_4)_6Mo_7O_{24} \cdot 4H_2O$ (marketed by Merck) in 400 cm$^3$ of demineralized water, and a solution (b) of uranyl nitrate by dissolving 50.2 g of $UO_2(NO_3)_2 6H_2O$ (marketed by Prolabo) in 50 cm$^3$ of demineralized water. The solution (b) was added to the solution (a) in a stirred reactor and was heated to approximately 80° C. The material was maintained at 80°–100° C. for approximately 2 hours and the resulting paste was dried at 120° C. for approximately 15 h; the product obtained was then calcined in air at 500° C. for 4 h.

The product thus prepared had a specific surface, measured by the B.E.T. method, of 2.4 m$^2$ g$^{-1}$.

10 g of this product were sprinkled slowly onto 65 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product was then again sprinkled onto the beads. These operations were continued alternately until all the product was coated. Drying was then carried out at 120° C. for 2 h and calcining at 480° C. for 6 h.

The catalyst (L) thus prepared contained 11.2% by weight of $UMo_{10}O_x$ deposited onto the clay beads.

EXAMPLE 59

Preparation Of A Catalyst Based On Cobalt Molybdate

An active catalytic phase of composition $CoMoO_4$ were prepared by the following operating procedure.

A solution (a) of ammonium heptamolybdate was prepared by dissolving 70.6 g of $(NH_4)_6Mo_7O_{24} \cdot 4H_2O$ (marketed by Merck) in 400 cm³ of demineralized water, and a solution (b) of cobalt nitrate by dissolving 116.4 g of $Co(NO_3)_2 \cdot 6H_2O$ in 150 cm³ of demineralized water. Solution (b) was added to the solution (a) in a stirred reactor and was heated to boiling. The resulting paste obtained was dried at 120° C. for approximately 15 h and was then calcined in air at 500° C. for 4 h.

The product thus prepared had a specific surface, measured by the B.E.T. method, of 7.7 m² g⁻¹.

10 g of this product were sprinkled slowly onto 50 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product was then again sprinkled onto the beads. These operations were continued alternately until all of the product was coated. Drying was then carried out at 120° C. for 2 h and calcining at 480° C. for 6 h.

The catalyst (M) thus prepared contained 11.7% by weight of $CoMoO_4$ deposited onto the clay beads.

EXAMPLE 60

Preparation Of A Catalyst Based On Cobalt Molybdate

An active catalytic phase of composition $CoMoO_4$ was prepared by the following operating procedure.

A solution (a) of ammonium heptamolybdate was prepared by the following operating procedure.

A solution (a) of ammonium heptamolybdate was prepared by dissolving 70.6 of $(NH_4)_6Mo_7O_{24} \cdot 4H_2O$ (marketed by Merck) in 400 cm³ of demineralized water, and a solution (b) of cobalt nitrate by dissolving 116.4 g of $Co(NO_3)_2 \cdot 6 H_2O$ in 150 cm³ of demineralized water. Solution (b) was added to the solution (a) in a stirred reactor and was heated to boiling. The resulting paste was filtered on sintered glass, dried at 120° C. for approximately 15 h and was then calcined in air at 500° C. for 4 h.

The product thus prepared had a specific surface, measured by the B.E.T. method, of 13 m² g⁻¹.

10 g of this product were sprinkled slowly onto 67 g of inert support particulates, i.e., clay beads having a mean diameter of 4.8 mm, preliminarily treated in a rotating pelletizer and moistened with glucose in aqueous solution at a concentration of 10%. As soon as the beads were dry on the outside, a small amount of the glucose solution was sprayed thereon. The product was then again sprinkled onto the beads. These operations were continued alternately until all of the product was coated. Drying was then carried out at 120° C. for 2 h and calcining at 480° C. for 6 h.

The catalyst (N) thus prepared contained 10% by weight of $CoMoO_4$ deposited onto the clay beads.

EXAMPLES 61 TO 65

Measurement of the performance of catalyst (L) at different temperatures and with different compositions of the reaction mixture:

The operating conditions employed were the following:

Hourly space velocity 1,000 h⁻¹

Total pressure=1.3 bar

The composition of the reaction mixture, the temperature and the results obtained are reported in Table XVII below:

TABLE XVII

| EXAMPLE | 61 | 62 | 63 | 64 | 65 |
|---|---|---|---|---|---|
| $C_3H_8$ (% vol) | 7.5 | 25 | 25 | 40 | 48 |
| $NH_3$ (% vol) | 15 | 25 | 10 | 15 | 9 |
| $O_2$ (% vol) | 15 | 10 | 25 | 15 | 18 |
| He (% vol) | 42.5 | 20 | 20 | 10 | 5 |
| T (°C.) | 460 | 430 | 460 | 460 | 480 |
| $DCC_3H_8$ (%) | 4 | 2 | 5 | 3 | 6 |
| SACN (%) | 19 | 15 | 13 | 13 | 18 |
| SACN + $C_3H_6$ (%) | 48 | 59 | 32 | 78 | 44 |
| $SCO_x$ (%) | 0 | 0 | 0 | 1 | 0 |

EXAMPLES 66 TO 69

Measurement of the performance of catalyst (M) at different temperatures and with different compositions of the reaction mixture:

The operating conditions employed were the following:

Hourly space velocity 1,000 h⁻¹

Total pressure 1.3 bar

The composition of the reaction mixture, the temperature and the results obtained are reported in Table XVIII below:

TABLE XVIII

| EXAMPLE | 66 | | 67 | | 68 | | 69 | | |
|---|---|---|---|---|---|---|---|---|---|
| $C_3H_8$ (% vol) | 7.5 | | 25 | | 40 | | 48 | | |
| $NH_3$ (% vol) | 15 | | 25 | | 15 | | 9 | | |
| $O_2$ (% vol) | 15 | | 10 | | 15 | | 18 | | |
| He (% vol) | 42.5 | | 20 | | 10 | | 5 | | |
| T (°C.) | 460 | 480 | 460 | 480 | 460 | 480 | 440 | 460 | 480 |
| $DCC_3H_8$ (%) | 8 | 17 | 6 | 6 | 7 | 11 | 6 | 10 | 16 |
| SACN (%) | 20 | 31 | 14 | 12 | 13 | 17 | 16 | 18 | 17 |
| SACN + $C_3H_6$ (%) | 76 | 75 | 59 | 67 | 83 | 84 | 73 | 79 | 75 |
| $SCO_x$ (%) | 0 | 0 | 0 | 0 | 0 | 1 | 0 | 1 | 5 |

EXAMPLES 70 TO 73

Measurement of the performance of catalyst (N) at different temperatures and with different compositions of the reaction mixture:

The operating conditions employed were the following:

Hourly space velocity 1,000 h⁻¹

Total pressure 1.3 bar

The composition of the reaction mixture, the temperature and the results obtained are reported in Table XIX below:

TABLE XIX

| EXAMPLE | 70 | 71 | | 72 | | 73 |
|---|---|---|---|---|---|---|
| $C_3H_8$ (% vol) | 7.5 | 25 | | 40 | | 48 |
| $NH_3$ (% vol) | 15 | 10 | | 15 | | 9 |
| $O_2$ (% vol) | 15 | 25 | | 15 | | 18 |
| He (% vol) | 42.5 | 20 | | 10 | | 5 |
| T (°C.) | 480 | 460 | 480 | 440 | 460 | 440 |
| $DCC_3H_8$ (%) | 11 | 8 | 15 | 6 | 11 | 5 |
| SACN (%) | 14 | 17 | 20 | 11 | 17 | 12 |
| SACN + $C_3H_6$ (%) | 84 | 82 | 76 | 83 | 83 | 82 |
| $SCO_x$ (%) | 2 | 0 | 4 | 0 | 1 | 0 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. In a process for the ammoxidation of an alkane into an α,β-ethylenically unsaturated nitrile, by reacting an acyclic alkane having 3 or more carbon atoms per molecule with ammonia and oxygen, the improvement comprising conducting said ammoxidation in vapor phase and in the presence of a solid catalyst, said solid catalyst comprising a catalytically effective amount of an active catalytic phase, said active catalytic phase consisting essentially of a mixed oxide of molybdenum and at least one metal selected from the group consisting of Mg, Ca, Mn, Fe, U, La, and Co.

2. The process according to claim 1, wherein said at least one metal is selected from the group consisting of Mn, Fe, Co, U and La.

3. The process according to claim 1, wherein said at least one metal is selected from the group consisting of Mg, Ca, U, La, Fe and Co.

4. The process as defined by claim 1, wherein said active catalytic phase consists essentially of manganese, uranyl, cobalt or iron molybdate.

5. The process as defined by claim 1, wherein said alkane is propane.

6. The process as defined by claim 1, wherein said alkane has from 3 to 12 carbon atoms.

7. The process as defined by claim 1, carried out in the presence of water vapor.

8. The process as defined by claim 1, comprising reacting gaseous admixture of from 5% to 70% of said alkane, from 3% to 50% of ammonia, and from 3% to 45% of oxygen.

9. The process as defined by claim 8, the composition of said gaseous admixture being outside of the explosive region thereof.

10. The process as defined by claim 8, said gaseous admixture comprising an inert diluent therefor.

11. The process as defined by claim 1, carried out at a temperature ranging from 350° to 550° C.

12. The process as defined by claim 1, carried out at a total pressure ranging from 1 to 6 bar.

13. The process as defined by claim 8, carried out at an hourly space velocity of said gaseous admixture ranging from 100 to 36,000 $h^{-1}$.

14. The process as defined by claim 1, said solid catalyst further comprising an inert support substrate having said active catalytic phase deposited thereon.

15. The process as defined by claim 1, said oxygen reactant comprising air.

16. The process as defined by claim 5, comprising the ammoxidation of propane into acrylonitrile and propylene.

17. A process for the ammoxidation of an alkane into an α,β-ethylenically unsaturated nitrile, by reacting an acyclic alkane having at least 3 carbon atoms per molecule with ammonia and oxygen, in vapor phase and in the presence of a solid catalyst, said solid catalyst comprising a catalytically effective amount of an active catalytic phase, said active catalytic phase consisting essentially of a mixed oxide of molybdenum and two metals selected from the group consisting of Mg, Ca, Mn, Fe, U, La, and Co.

18. In a process for the ammoxidation of an alkane into an α,β-ethylenically unsaturated nitrile, by reacting an acyclic alkane having 3 or more carbon atoms per molecule with ammonia and oxygen, the improvement comprising conducting said ammoxidation in vapor phase and in the presence of a solid catalyst, said solid catalyst comprising a catalytically effective amount of an active catalytic phase, said active catalytic phase consisting essentially of an orthomolybdate of at least one metal selected from the group consisting of Mg, Ca, Mn, Fe, U, La, and Co.

* * * * *